(12) United States Patent
Gu et al.

(10) Patent No.: US 9,668,715 B2
(45) Date of Patent: Jun. 6, 2017

(54) ACOUSTIC PROBE AND METHOD OF MANUFACTURING THE SAME

(71) Applicant: SAMSUNG MEDISON CO., LTD., Gangwon-do, Hongcheon-gun (KR)

(72) Inventors: Jin-ho Gu, Gangwon-do (KR); Jae-yk Kim, Gangwon-do (KR); Gil-ju Jin, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 374 days.

(21) Appl. No.: 14/153,898

(22) Filed: Jan. 13, 2014

(65) Prior Publication Data

US 2015/0051493 A1    Feb. 19, 2015

(30) Foreign Application Priority Data

Aug. 19, 2013    (KR) ........................ 10-2013-0098126

(51) Int. Cl.
*A61B 8/00* (2006.01)
*B06B 1/06* (2006.01)

(52) U.S. Cl.
CPC .......... *A61B 8/4444* (2013.01); *B06B 1/0622* (2013.01); *Y10T 29/42* (2015.01)

(58) Field of Classification Search
CPC ......... B06B 1/0622; G10K 11/02; A61B 8/44; A61B 8/4444; Y10T 29/42
USPC ........................................ 310/334, 335, 344
See application file for complete search history.

(56) References Cited

U.S. PATENT DOCUMENTS

| | | | |
|---|---|---|---|
| 7,728,487 B2 * | 6/2010 | Adachi | A61B 8/4483 310/309 |
| 8,410,666 B2 | 4/2013 | Shikata et al. | |
| 8,604,671 B2 * | 12/2013 | Shikata | B06B 1/0629 310/334 |
| 2003/0189391 A1 * | 10/2003 | Shimizu | G10K 11/002 310/334 |
| 2007/0276248 A1 * | 11/2007 | Saito | A61B 8/546 600/459 |
| 2010/0156243 A1 | 6/2010 | Weekamp et al. | |
| 2010/0317972 A1 * | 12/2010 | Baumgartner | G10K 11/002 600/459 |
| 2011/0295124 A1 | 12/2011 | Shikata et al. | |
| 2011/0316387 A1 * | 12/2011 | Togasaki | B06B 1/0622 310/334 |

FOREIGN PATENT DOCUMENTS

WO    2012/085724 A1    6/2012

OTHER PUBLICATIONS

Extended European Search Report dated Jan. 31, 2017, issued in European Application No. 13196205.2.

\* cited by examiner

*Primary Examiner* — Shawki S Ismail
*Assistant Examiner* — Bryan Gordon
(74) *Attorney, Agent, or Firm* — McDermott Will & Emery LLP (57) ABSTRACT

Provided are an acoustic probe and a method of manufacturing the acoustic probe including a chip module substrate, a piezoelectric unit for cross-converting ultrasound and an electric signal while the piezoelectric unit is vibrating, and a connection unit for supporting the piezoelectric unit and electrically connecting the piezoelectric unit and the chip module substrate.

11 Claims, 9 Drawing Sheets

ACOUSTIC PROBE AND METHOD OF MANUFACTURING THE SAME

RELATED APPLICATIONS

This application claims the benefit of Korean Patent Application No. 10-2013-0098126, filed on Aug. 19, 2013, in the Korean Intellectual Property Office, the disclosure of which is incorporated herein in its entirety by reference.

BACKGROUND

1. Field

One or more embodiments of the present invention relate to an acoustic probe and a method of manufacturing the same.

2. Description of the Related Art

In general, an ultrasound diagnosis apparatus irradiates ultrasound into a target object of a living body of a person or animal, displays a tomography image of tissue or tissues in the living body on a monitor by detecting an echo signal reflected from the target object, and provides information for diagnosing the target object.

Here, the ultrasound diagnosis apparatus includes an acoustic probe for transmitting the ultrasound into the target object and receiving the echo signal from the target object. The acoustic probe is embedded in the ultrasound diagnosis apparatus and includes a piezoelectric unit for cross-converting an ultrasound signal and an electric signal. In general, the piezoelectric unit includes an array of a plurality of piezoelectric elements.

Thus, the ultrasound diagnosis apparatus having the aforementioned structure irradiates the ultrasound into the target object, converts the echo signal of the reflected ultrasound into an electric signal, transmits the electric signal to an image processing unit, and then generates an image by using a signal received from the image processing unit. The ultrasound diagnosis apparatus, which uses via the aforementioned procedure, is a valuable apparatus for medical purposes including detection of foreign materials in the living body, damage measurement, tumor observation, fetus observation or the like.

Various methods are studied to connect the piezoelectric elements to a substrate having a chip for processing the electrical signal. For example, the substrate and the piezoelectric elements may be attached to one another by using ball-shape bumps or column-shape adhesion layers. However, it is difficult to align the bumps or the adhesion layers, a process using the bumps or the adhesion layers is complicated, and the bumps or the adhesion layers have weak durability.

SUMMARY

One or more embodiments of the present invention include an acoustic probe that is easily manufactured and has improved durability and a method of manufacturing the acoustic probe.

Additional aspects will be set forth in part in the description which follows and, in part, will be apparent from the description, or may be learned by practice of the presented embodiments.

According to one or more embodiments of the present invention, an acoustic probe includes a chip module substrate; a piezoelectric unit for cross-converting ultrasound and an electric signal while the piezoelectric unit is vibrating; and a connection unit for supporting the piezoelectric unit and electrically connecting the piezoelectric unit and the chip module substrate.

The connection unit may include a first surface electrically connected to the chip module substrate and a second surface electrically connected to the piezoelectric unit, wherein a size of the first surface and a size of the second surface are different from each other.

The size of the first surface may be less than the size of the second surface.

Acoustic impedance of the connection unit may be greater than acoustic impedance of the piezoelectric unit.

The connection unit may include at least one of tungsten carbide and graphite.

At least one of a greatest thickness and a smallest thickness of the connection unit may be $\lambda/(2n)$, where $\lambda$ is a frequency of ultrasound emitted from the piezoelectric unit, and n is a natural number.

The piezoelectric unit may include a plurality of piezoelectric elements that are spaced apart from one other, and the connection unit may include a plurality of connection elements that are spaced apart from one other and support the plurality of piezoelectric elements, respectively.

At least one of the plurality of connection elements may be stepped at least once.

A longitudinal cross-section of at least one of the plurality of connection elements may have a T-shape.

The acoustic probe may further include a bonding material disposed between the connection unit and the chip module substrate.

The bonding material may include a conductive material.

The chip module substrate may include an ultrasound-backing material.

The acoustic probe may further include an ultrasound-backing unit disposed at a rear side of the chip module substrate and absorbing a part of ultrasound that is generated by the piezoelectric unit.

According to one or more embodiments of the present invention, a method of manufacturing an acoustic probe includes operations of forming at least one protruding portion by partially sawing a base layer; bonding the at least one protruding portion to the chip module substrate; forming a piezoelectric layer on a surface of the base layer which is opposite to another surface of the base layer on which the at least one protruding portion is formed; and forming a plurality of piezoelectric elements and a plurality of connection elements by sawing the piezoelectric layer and the base layer.

Acoustic impedance of the base layer may be greater than acoustic impedance of the piezoelectric layer.

A bonding material may be formed on the at least one protruding portion.

At least one of the plurality of connection elements may be stepped at least once.

A longitudinal cross-section of at least one of the plurality of connection elements may have a T-shape.

The base layer may include at least one of tungsten carbide and graphite.

A substrate of the chip module substrate may be formed of an ultrasound-backing material.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to the like elements throughout, and redundant explanations are omitted. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Throughout the specification, a term 'target object' may include a person, animal, or a part of a person or animal. For example, the target object may include organs such as the liver, the heart, the womb, the brain, the breast, the abdominal region, etc., or a blood vessel. Throughout the specification, a "user" may be a medical expert including a doctor, a nurse, a medical laboratory technologist, a medical image expert, a technician repairing medical equipments, or the like.

Figure 1:
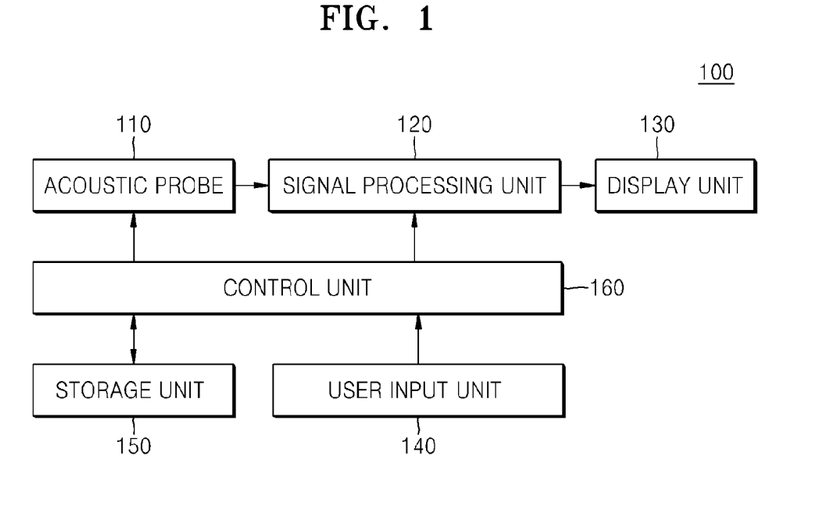
FIG. 1 is a block diagram of an ultrasound diagnosis apparatus according to an embodiment of the present invention.

FIG. 1 is a block diagram of an ultrasound diagnosis apparatus 100 according to an embodiment of the present invention. Referring to FIG. 1, the ultrasound diagnosis apparatus 100 includes an acoustic probe 110 for transmitting and receiving ultrasound, a signal processing unit 120 for generating an image by processing a signal applied from the acoustic probe 110, a display unit 130 for displaying the image, a user input unit 140 for receiving a user input, a storage unit 150 for storing various types of information, and a control unit 160 for controlling all operations of the ultrasound diagnosis apparatus 100.

The acoustic probe 110 transmits ultrasound to a target object and receives an echo signal of the ultrasound reflected from the target object. The acoustic probe 110 will be described in detail at a later time.

The signal processing unit 120 generates an ultrasound image by processing ultrasound data generated by the acoustic probe 110. The ultrasound image may be at least one of an image obtained during a brightness mode (B mode) in which magnitude of an echo signal of ultrasound reflected from a target object is expressed as a brightness; an image obtained during a Doppler mode in which an image of a moving target object is shown as a spectrum image by using a Doppler effect; an image obtained during a motion mode (M mode) in which motion of a target object according to time is shown at a constant location; an image obtained during an elasticity mode in which a difference between a case of applying compression to a target object and a case of not applying the compression to the target object is expressed as an image; and an image obtained during a color mode (C mode) in which a speed of a moving target object is expressed as a color by using a Doppler effect. One of currently usable methods of generating an ultrasound image may be applied to one or more embodiments of the present invention, and thus, detailed descriptions thereof are omitted here. Accordingly, in the present embodiment, the ultrasound image may include images obtained in dimensional modes such as one-dimensional (1D), two-dimensional (2D), three-dimensional (3D), four-dimensional (4D), or the like.

The display unit 130 displays information processed in the ultrasound diagnosis apparatus 100. For example, the display unit 130 may display the ultrasound image generated by the signal processing unit 120, and may also display a graphical user interface (GUI) for requesting a user input.

The display unit 130 may include at least one of a liquid crystal display (LCD), a thin film transistor-liquid crystal display (TFT-LCD), an organic light-emitting display device, a flexible display, a 3D display, and an electrophoretic display. In another embodiment, the ultrasound diagnosis apparatus 100 may include at least two display units 130.

The user input unit 140 means a unit used by a user to input data so as to control the ultrasound diagnosis apparatus 100. The user input unit 140 may include a key pad, a mouse, a touch panel, a trackball, or the like. The user input unit 140 in one or more embodiments of the present invention is not limited thereto, and thus may further include various input units such as a jog wheel, a jog switch, or the like.

A touch panel may detect not only an actual touch, but may also detect a proximate touch. The actual touch means a case in which a pointer actually touches a screen, and the proximate touch means a case in which the pointer approaches the screen but does not actually touch the screen. Furthermore, in the case of the proximate touch, a predetermined distance is maintained between the pointer and the screen. In the present embodiment, the pointer is a tool used for actually touching or proximately touching a predetermined portion of the touch panel. An example of the tool includes a stylus pen, a part of a body such as a finger, or the like.

The touch panel and the display unit 130 may form a multiple-layer structure to embody a touch screen. The touch screen may be variously embodied as a capacitive type touch screen, a pressure resistive type touch screen, an infrared beam sensing type touch screen, a surface acoustic wave type touch screen, an integral strain gauge type touch screen, a piezoelectric effect type touch screen, or the like. Since the touch panel performs functions of both display unit 130 and user input unit 140, the touch panel has excellent utilization.

Although not illustrated, in order to detect the actual touch or the proximate touch on the touch pad, the touch pad may internally or externally have various sensors. An example of the sensor used to detect the actual touch or the proximate touch on the touch pad may include a tactile sensor. The tactile sensor detects a contact of a specific object due to having a sensitivity that is equal to or greater than that of human touch. The tactile sensor may detect various types of information, such as the roughness of a contact surface, the hardness of the contact object, the temperature of a contact point, or the like.

Also, another example of the sensor used to detect the actual touch or the proximate touch on the touch pad may include a proximity sensor. The proximity sensor detects the existence of an object that approaches a predetermined detection surface or that exists nearby, by using a force of an electro-magnetic field or infrared rays, without using a mechanical contact. Examples of the proximity sensor include a transmission-type photoelectric sensor, a direction reflection-type photoelectric sensor, a mirror reflection-type photoelectric sensor, a high frequency oscillation-type proximity sensor, a capacity-type proximity sensor, a magnetic proximity sensor, an infrared-type proximity sensor, or the like.

The storage unit 150 stores various types of information processed in the ultrasound diagnosis apparatus 100. For example, the storage unit 150 may store medical data such as an image or the like related to diagnosing a target object, and may store an algorithm or a program, which is performed in the ultrasound diagnosis apparatus 100.

The storage unit 150 may include a flash memory-type storage medium, a hard disk-type storage medium, a multimedia card micro-type storage medium, a card type memory (e.g., an SD card memory or an XD card memory), a Random Access Memory (RAM), a Static Random Access Memory (SRAM), a Read-Only Memory (ROM), an Electrically Erasable Programmable Read-Only Memory (EEPROM), a Programmable Read-Only Memory (PROM), a magnetic memory, a magnetic disc, and an optical disc. Also, the ultrasound diagnosis apparatus 100 may operate a web storage system that performs a storing function of the storage unit 150 over the Internet.

The control unit 160 controls all operations of the ultrasound diagnosis apparatus 100. That is, the control unit 160 may control operations performed by the acoustic probe 110, the signal processing unit 120, the display unit 130, or the like shown in FIG. 1. For example, the control unit 160 may control the signal processing unit 120 to generate an image by using a user command that is input via the user input unit 140 or by using the program stored in the storage unit 150. Also, the control unit 160 may control the display unit 130 to display the image generated by the signal processing unit 120.

Figure 2:
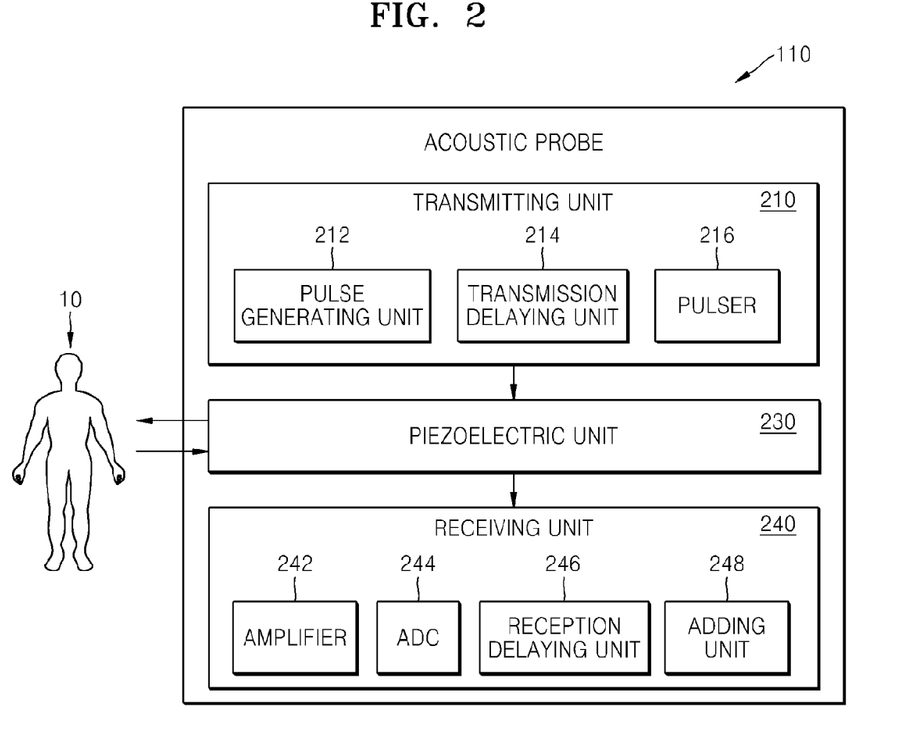
FIG. 2 is a block diagram of an acoustic probe shown in FIG. 1.

FIG. 2 is a block diagram of the acoustic probe 110 shown in FIG. 1. Referring to FIG. 2, the acoustic probe 110 is a device capable of transmitting ultrasound to a target object 10 and generating ultrasound data by receiving an echo signal of the ultrasound reflected from the target object 10, and may include a transmitting unit 210, a piezoelectric unit 230, and a receiving unit 240.

The transmitting unit 210 supplies a driving signal to the piezoelectric unit 230. The transmitting unit 210 may include a pulse generating unit 212, a transmission delaying unit 214, and a pulser 216.

The pulse generating unit 212 generates rate pulses for generating transmission ultrasound according to a pulse repetition frequency (PRF). The transmission delaying unit 214 applies a delay time for determining transmission directionality to the rate pulses generated by the pulse generating unit 212. Each of the rate pulses having the delay time applied thereto corresponds to each of a plurality of piezoelectric elements 232 included in the piezoelectric unit 230. The pulser 216 applies the driving signal or a driving pulse to the piezoelectric unit 230 based on timing that corresponds to each of the rate pulses having the delay time applied thereto.

The piezoelectric unit 230 transmits the ultrasound to the target object 10 in response to the driving signal supplied from the transmitting unit 210, and receives the echo signal of the ultrasound reflected from the target object 10. The piezoelectric unit 230 may include the piezoelectric elements 232 that convert an electric signal to acoustic energy or vice versa.

The receiving unit 240 may generate the ultrasound data by processing a signal received from the piezoelectric unit 230, and may include an amplifier 242, an analogue-to-digital converter (ADC) 244, a reception delaying unit 246, and an adding unit 248.

The amplifier 242 amplifies the signal received from the piezoelectric unit 230, and the ADC 244 performs analogue-to-digital conversion on the amplified signal. The reception delaying unit 246 applies a delay time for determining reception directionality to the digitized signal. The adding unit 248 generates the ultrasound data by adding signals processed by the reception delaying unit 246. Due to the addition of signals by the adding unit 248, a reflection component in a direction defined by the reception directionality may be emphasized.

The transmitting unit 210 and the receiving unit 240 of the acoustic probe 110 may be formed as at least one chip on a substrate. Here, the substrate may be formed of silicon (Si), ceramic, or a polymer-based material. Also, the substrate may be formed of a ultrasound-backing material that absorbs ultrasound. Each of blocks in the transmitting unit 210 and the receiving unit 240 may be formed as one chip, at least two of the blocks may be formed as one chip, and one chip may be formed to correspond to one piezoelectric element. Therefore, a substrate that includes at least one of the transmitting unit 210 and the receiving unit 240 is referred to as a chip module substrate. The chip module substrate means not only a substrate including all chips of the acoustic probe 110 but also means a substrate including some of the chips of the acoustic probe 110.

The acoustic probe 110 may further include more elements of the signal processing unit 120, more elements of the display unit 130, more elements of the user input unit 140, or the like, in addition to the transmitting unit 210 and the receiving unit 240.

Figure 3:
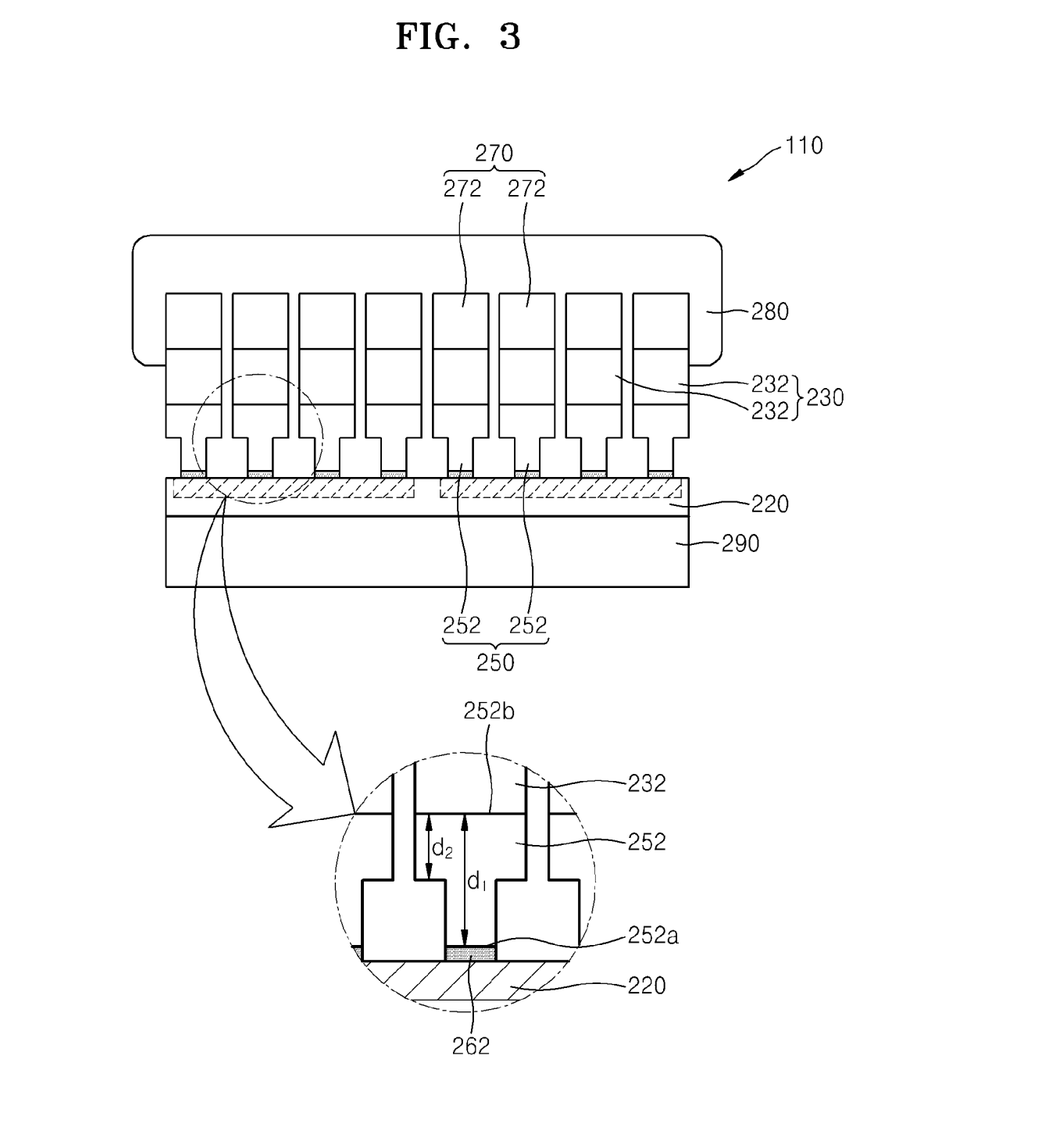
FIG. 3 schematically illustrates a physical structure of the acoustic probe shown in FIG. 2.

FIG. 3 schematically illustrates a physical structure of the acoustic probe 110 shown in FIG. 2. As illustrated in FIG. 3, the acoustic probe 110 may include the chip module substrate 220, the piezoelectric unit 230 for cross-converting ultrasound and an electric signal while the piezoelectric unit 230 vibrates, and a connection unit 250 for supporting the piezoelectric unit 230 and electrically connecting the piezoelectric unit 230 and the chip module substrate 220. As described above, the chip module substrate 220 means the substrate including at least one chip that processes an electric signal. For example, the chip module substrate 220 includes at least one chip for performing operations by the receiving unit 240 and the transmitting unit 210. The chip module substrate 220 may be a customized semiconductor (i.e., an application specific integrated circuit (ASIC)), but one or more embodiments of the present invention are not limited thereto.

The piezoelectric unit 230 is formed of the piezoelectric elements 232 that cross-convert the ultrasound and the electric signal while the piezoelectric elements 232 vibrate. The piezoelectric elements 232 may be spaced apart from each other. The piezoelectric elements 232 may be formed by splitting a piezoelectric material. For example, the piezoelectric elements 232 may be formed by using a dicing-process on the piezoelectric material that extends lengthwise. However, the manufacture of the piezoelectric elements 232 is not limited to the aforementioned method, and thus, the piezoelectric elements 232 may be formed by pressing metal or a conductive material including metal or by using various other methods. The piezoelectric material may include, but is not limited to, a piezoelectric ceramic, a single crystal material, or a composite piezoelectric material formed by compounding a polymer material and any of the aforementioned materials causing a piezoelectric effect.

The connection unit 250 supports the piezoelectric unit 230 and electrically connects the piezoelectric unit 230 and the chip module substrate 220. The connection unit 250 may include a plurality of connection elements 252 that are spaced apart from each other and support the piezoelectric elements 232, respectively. In the present embodiment, the connection elements 252 support the piezoelectric elements 232, respectively, but one or more embodiments of the present invention are not limited thereto. That is, one connection element 252 may support several piezoelectric elements 232, or at least two connection elements 252 may support one piezoelectric element 232. The connection unit 250 may be formed of a conductive material, and the impedance of the connection unit 250 may be greater than the impedance of the piezoelectric unit 230. Therefore, ultrasound emitted toward a rear side of the piezoelectric unit 230 may be reflected from the connection unit 250 and then may be emitted toward a front side of the piezoelectric unit 230. As a result, an efficiency of ultrasound emission may be highly improved. The connection unit 250 may be formed of a material such as tungsten carbide, graphite, or the like, which has conductivity and high acoustic impedance.

Also, the connection unit 250 may include a first surface 252a electrically connected to the chip module substrate 220, and a second surface 252b electrically connected to the piezoelectric unit 230. Sizes of the first surface 252a and the second surface 252b may be different from each other, and the size of the first surface 252a may be equal to or less than the size of the second surface 252b. Since the first surface 252a has a small area so as to be connected to only a required region of the chip module substrate 220, deterioration in motion of the piezoelectric unit 230 may be prevented, and since the second surface 252b supports an entire bottom portion of the piezoelectric unit 230, the piezoelectric unit 230 may further stably vibrate.

In more detail, at least one of the connection elements 252 may be stepped at least once. For example, a longitudinal cross-section of at least one of the connection elements 252 may have a T-shape. At least one of a greatest thickness d1 and a smallest thickness d2 of the connection element 252 may be about $\lambda/(2n)$ (where, $\lambda$ is a frequency of ultrasound emitted from the piezoelectric unit 230, and n is a natural number). In more detail, when the greatest thickness d1 of the connection element 252 is about $\lambda/(2n)$, the smallest thickness d2 of the connection element 252 may be one of about $\lambda/8$ and about $\lambda/16$. Therefore, ultrasound incident on the connection element 252 may be reflected back toward the front side of the piezoelectric unit 230. A bonding material 262 may be coated on the first surface 252a of the connection element 252, so that the connection element 252 may be further attached to the chip module substrate 220 more easily. The bonding material 262 may be a conductive material including tin (Sn), silver (Ag), lead (Pb), or the like.

The acoustic probe 110 may further include a matching unit 270 for matching acoustic impedance of ultrasound generated by the piezoelectric unit 230 with acoustic impedance of a target object. The matching unit 270 is disposed on a front surface of the piezoelectric unit 230, alters, in a stepwise manner, the acoustic impedance of the ultrasound generated by the piezoelectric unit 230, which causes the acoustic impedance of the ultrasound to be similar to the acoustic impedance of the target object. Here, the front surface of the piezoelectric unit 230 may indicate a surface of the piezoelectric unit 230 which is the most adjacent to the target object from among surfaces of the piezoelectric unit 230 while the ultrasound is emitted to the target object, and a rear surface of the piezoelectric unit 230 may indicate a surface of the piezoelectric unit 230 which is opposite to the front surface.

The matching unit 270 may extend lengthwise along the front surface of the piezoelectric unit 230, but one or more embodiments of the present invention are not limited thereto, and thus, the matching unit 270 may be partially formed on the piezoelectric unit 230. In the present embodiment, the matching unit 270 has a single-layered structure. However, in another embodiment, the matching unit 270 may have a multi-layered structure.

The acoustic probe 110 may further include an acoustic lens 280 for focusing the ultrasound. The acoustic lens 280 is disposed on the front surface of the piezoelectric unit 230, and functions to focus the ultrasound generated by the piezoelectric unit 230. The acoustic lens 280 may be formed of a material such as a silicon rubber having an acoustic impedance that is similar to the acoustic impedance of the target object. A central portion of the acoustic lens 280 may be convex or flat. The acoustic lens 280 may have various shapes according to designs of manufacturers.

The acoustic probe 110 may include a ultrasound-backing unit 290 that absorbs ultrasound transmitted in a direction away from the target object. The ultrasound-backing unit 290 may support the chip module substrate 220 at a rear side of the chip module substrate 220. Additionally, the ultrasound-backing unit 290 may absorb the ultrasound that is transmitted toward the rear side of the chip module substrate 220 and that is not directly used in a test or a diagnosis. In the embodiment of FIG. 3, the ultrasound-backing unit 290 is separately formed from the chip module substrate 220, but one or more embodiments of the present invention are not limited thereto. The substrate of the chip module substrate 220 may be formed of a ultrasound-backing material. By doing so, the chip module substrate 220 may perform a function of the ultrasound-backing unit 290.

Figure 4A:
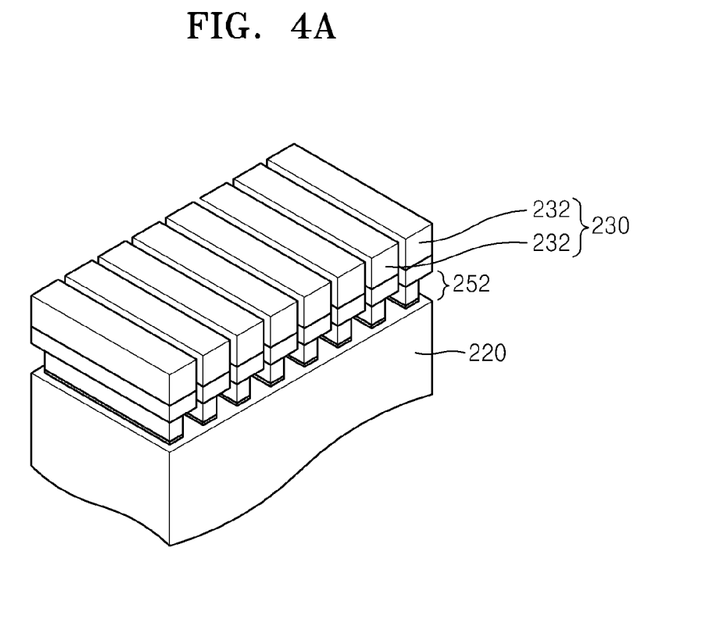
FIGS. 4A and 4B illustrate array states of piezoelectric elements in a piezoelectric unit, according to embodiments of the present invention.

FIGS. 4A and 4B illustrate array states of the piezoelectric elements 232 in the piezoelectric unit 230, according to embodiments of the present invention. As illustrated in FIG. 4A, the piezoelectric elements 232 may be one-dimensionally arrayed on front surfaces of the connection elements 252 along a longitudinal direction of the piezoelectric unit 230. This one-dimensionally array of the piezoelectric elements 232 may be referred as a 1D piezoelectric unit. The 1D piezoelectric unit may have a linear array or a curved array. An array shape may vary according to a purpose of a designer. The 1D piezoelectric unit is easily manufactured, thereby keeping manufacturing costs low. However, it is difficult to realize a 3D image by using the 1D piezoelectric unit.

Figure 4B:
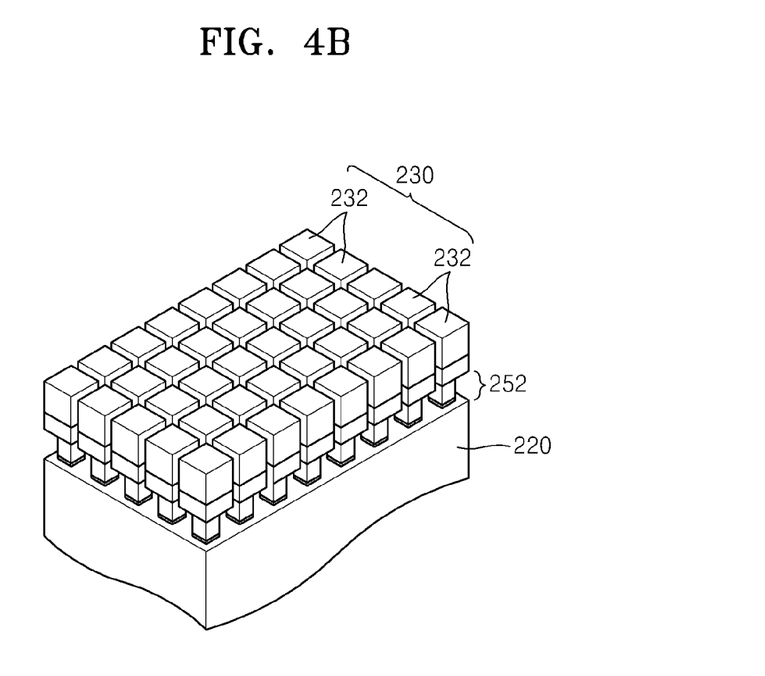

As illustrated in FIG. 4B, the piezoelectric elements 232 may be two-dimensionally arrayed along not only the longitudinal direction of the piezoelectric unit 230, but also along a direction vertical to the longitudinal direction. This two-dimensionally array of the piezoelectric elements 232 may be referred as a 2D piezoelectric unit. The 2D piezoelectric unit may have a linear array or a curved array. An array shape may vary according to a purpose of a designer. The 2D piezoelectric unit appropriately delays an input time of signals that are input to the piezoelectric elements 232, respectively, and then transmits the signals to a target. Thus, the 2D piezoelectric unit may obtain a 3D image by using echo signals. As the number of the piezoelectric elements 232 is increased, resolution of an ultrasound image may also be improved.

FIGS. 5A through 5G are reference diagrams illustrating a method of manufacturing the acoustic probe 110, according to an embodiment of the present invention.

Figure 5A:
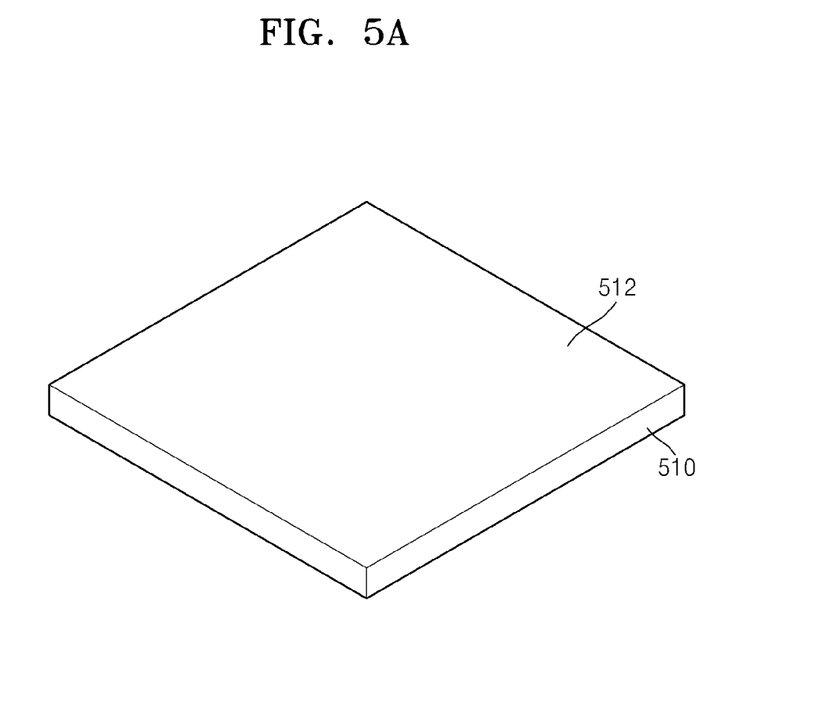
FIGS. 5A through 5G are reference diagrams illustrating a method of manufacturing the acoustic probe, according to an embodiment of the present invention.

As illustrated in FIG. 5A, a base layer 510 is prepared. The base layer 510 may be formed of a conductive material, and acoustic impedance of the base layer 510 may be greater than acoustic impedance of other elements of the base layer 510, e.g., acoustic impedance of the piezoelectric unit 230. The base layer 510 may include at least one of tungsten carbide and graphite.

Figure 5B:
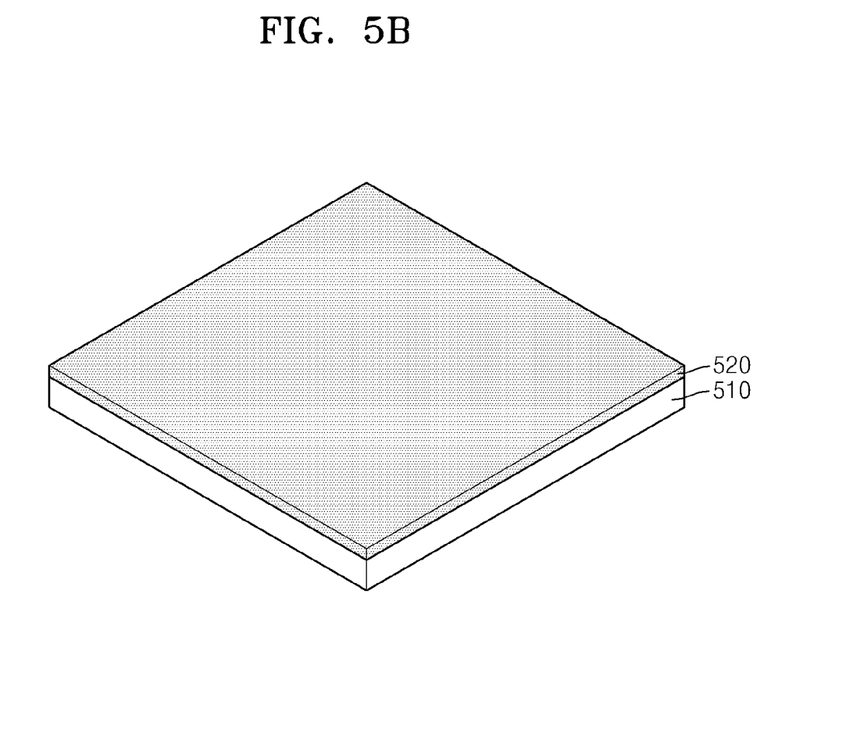

As illustrated in FIG. 5B, a bonding material 520 may be coated on a first surface of the base layer 510. The bonding material 520 may be a conductive material such as Sn, Ag, or the like.

Figure 5C:
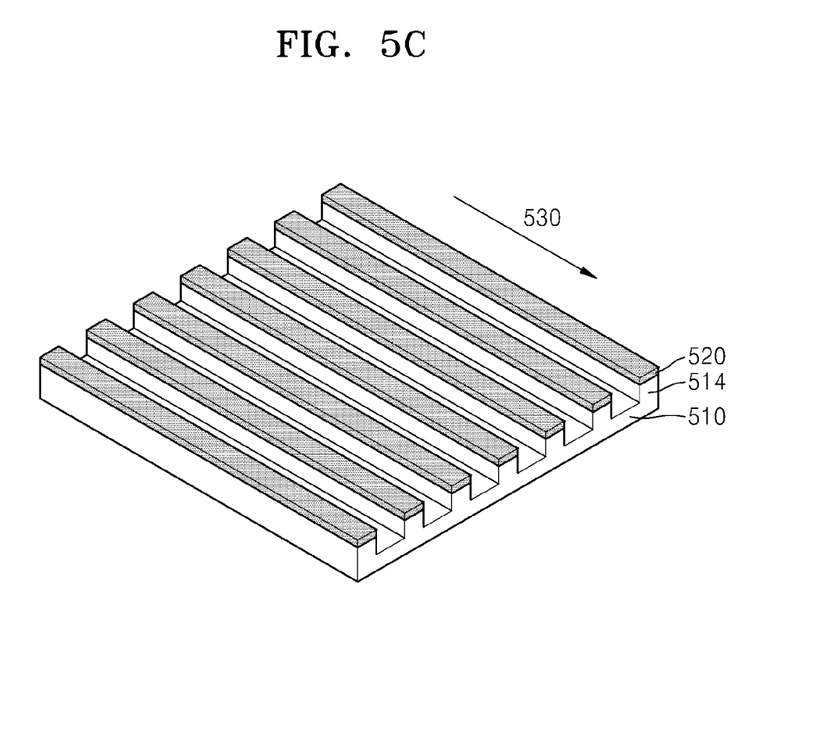
Figure 5D:
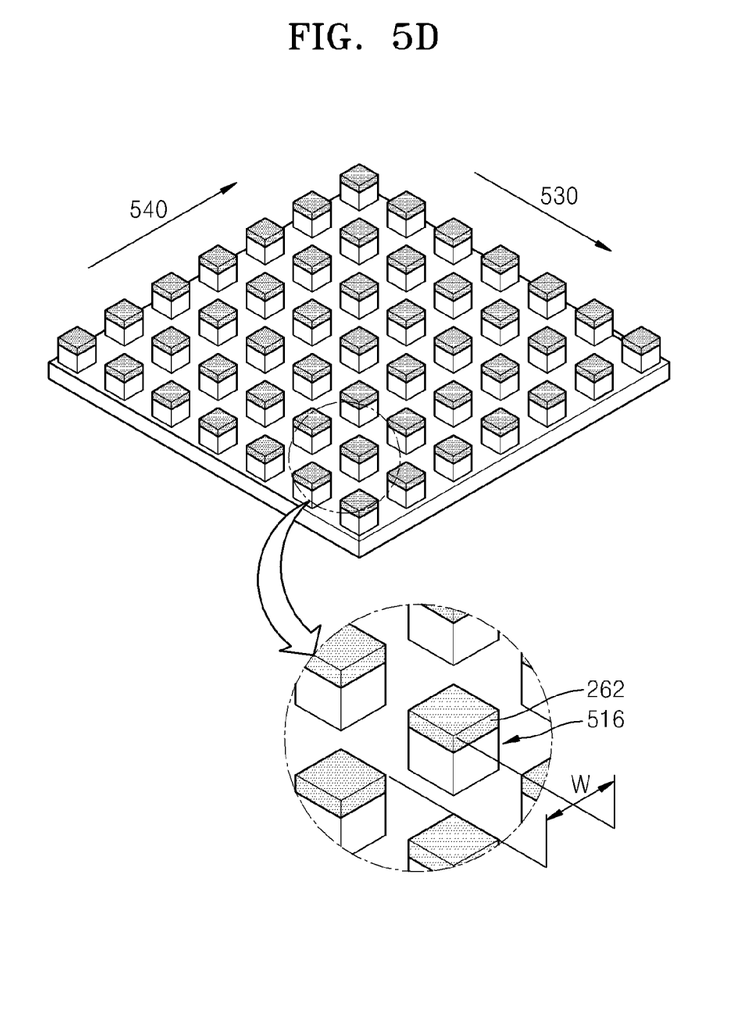

Afterward, as illustrated in FIGS. 5C and 5D, the base layer 510 may be partially sawed so that one or more protruding portions 514 and 516 may be formed. In order to generate a connection unit to be applied to the 1D piezoelectric unit, as illustrated in FIG. 5C, the base layer 510 may be partially sawed in only a first direction 530 so that the protruding portions 514 may be formed. In order to generate a connection unit to be applied to the 2D piezoelectric unit, as illustrated in FIG. 5D, the base layer 510 may be partially sawed in first and second directions 530 and 540 so that the protruding portions 516 may be formed. A sawing width w1 is related to a distance between chips of the chip module substrate 220. Hereinafter, for convenience of description, a method of manufacturing the acoustic probe 110 including the 2D piezoelectric unit is described below. Since the base layer 510 is partially sawed, the bonding material 262 remains only on the protruding portions 516.

Figure 5E:
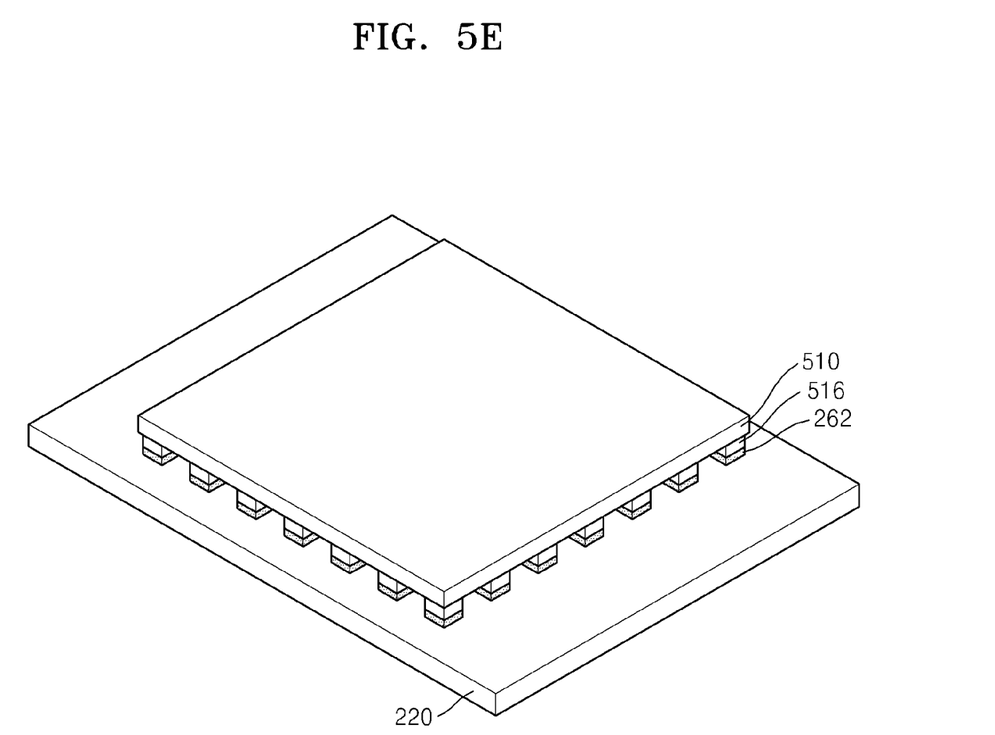

Afterward, as illustrated in FIG. 5E, the bonding material 262 is bonded to the chip module substrate 220 so that the base layer 510 is attached to the chip module substrate 220. For example, the base layer 510 may be attached to the chip module substrate 220 by using a hot pressing method. Since the bonding material 262 is coated on the base layer 510, the attachment of the base layer 510 to the chip module substrate 220 may be easily achieved since the bonding material 262 is bonded to a corresponding electrode pad of the chip module substrate 220.

Figure 5F:
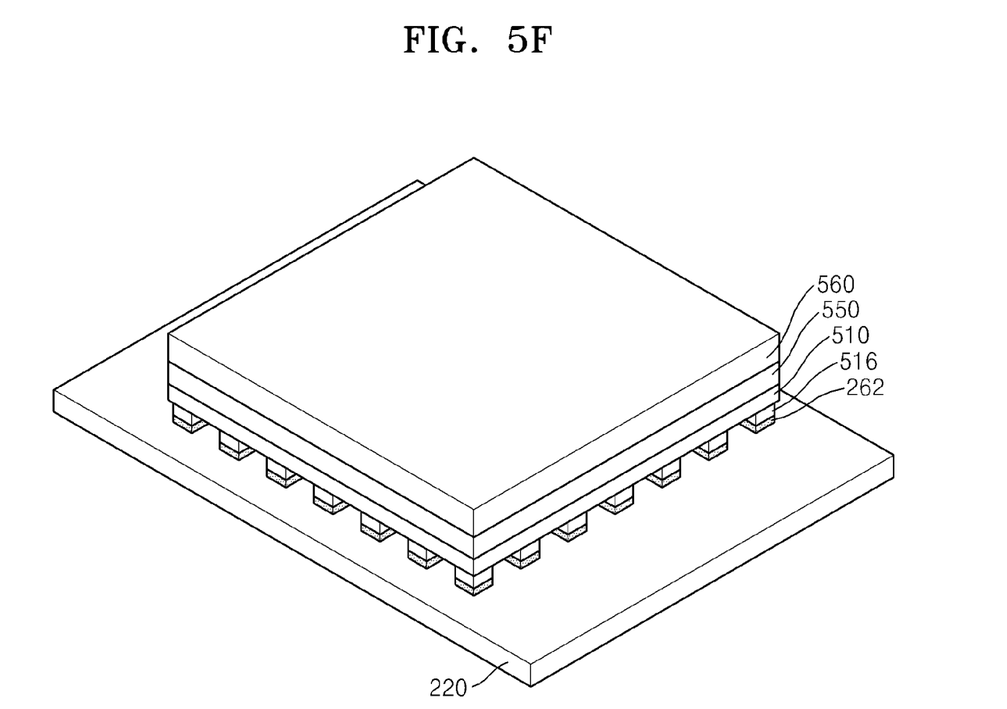
Figure 5G:
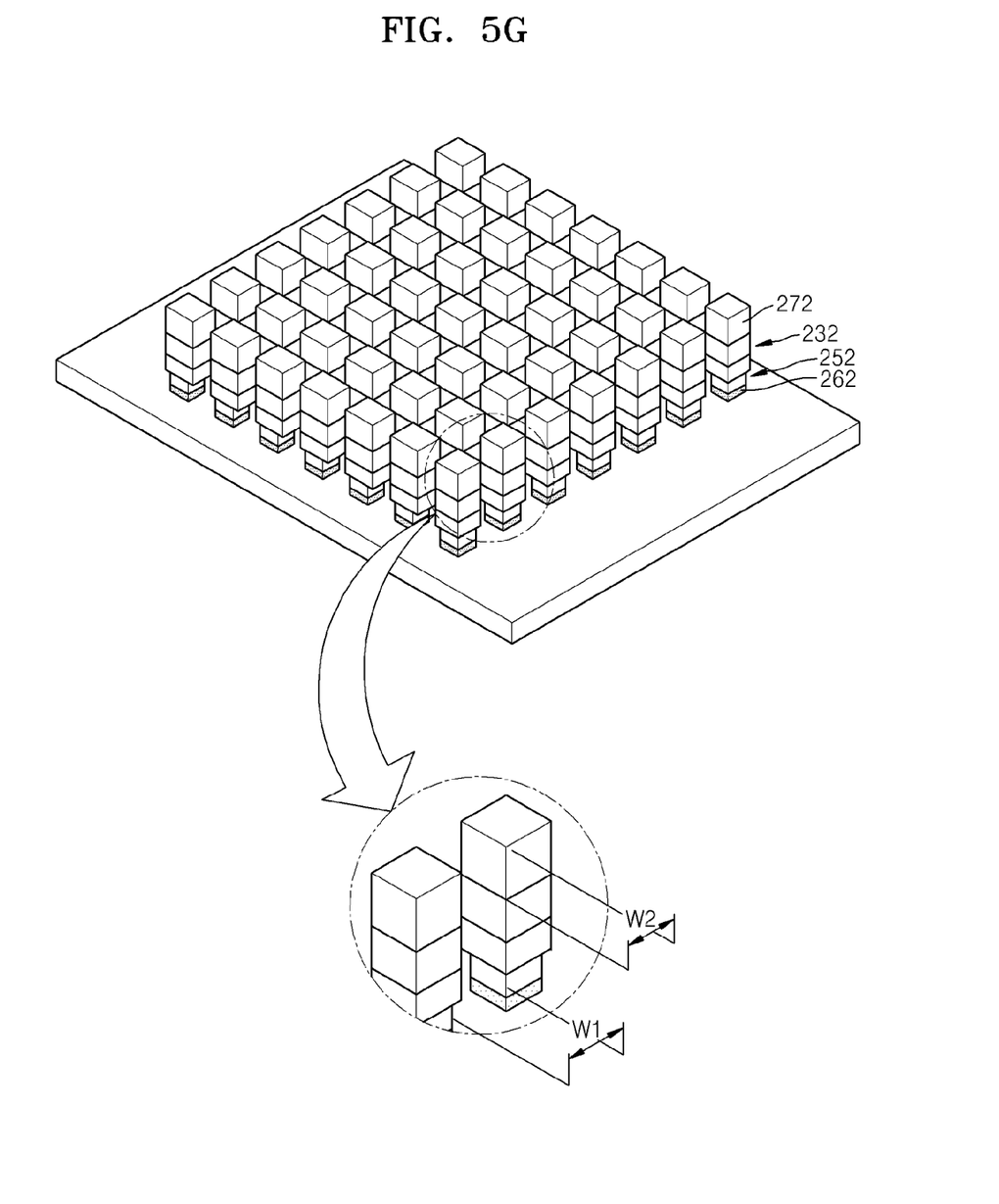

As illustrated in FIG. 5F, a piezoelectric layer 550 and a matching layer 560 may be sequentially stacked on a second surface of the base layer 510. The matching layer 560 may be formed of a plurality of layers having different acoustic impedances. Afterward, as illustrated in FIG. 5G, the matching layer 560, the piezoelectric layer 550, and the base layer 510 may be sawed. The matching layer 560, the piezoelectric layer 550, and the base layer 510 may be sawed to form matching elements 272, piezoelectric elements 232, and connection elements 252, respectively. A sawing width w2 that is related to forming the matching elements 272, the piezoelectric elements 232, and the connection elements 252 may be equal to or less than the sawing width w1 related to forming the protruding portions 514 and 516 of the base layer 510. By doing so, a side portion of each of the connection elements 252 may have a stepped shape. That is, since the second surface 252b of the connection element 252 which supports the piezoelectric element 232 is greater than the first surface 252a of the connection element 252 which contacts the chip module substrate 220, the connection element 252 may stably support the piezoelectric element 232 without deteriorating the motion of the piezoelectric unit 230.

As described above, the piezoelectric unit 230 is attached to the chip module substrate 220 by using the base layer 510, so that the manufacturing procedure may be simplified, and a distance between the piezoelectric unit 230 and the chip module substrate 220 may be constant.

Although not illustrated, the acoustic lens 280 may be stacked on the matching unit 270. Also, the piezoelectric layer 550 and the base layer 510 may be sawed to be formed as the piezoelectric elements 232 and the connection elements 252, respectively, and the matching elements 272 and the acoustic lens 280 may be stacked on the piezoelectric elements 232. In addition, the ultrasound-backing unit 290 may be formed below the chip module substrate 220.

As described above, according to the one or more of the above embodiments of the present invention, the acoustic probe has a structure in which a conductive material having high acoustic impedance is disposed between the piezoelectric elements and the chip module substrate, so that the acoustic probe may have improved durability.

According to the one or more of the above embodiments of the present invention, since the piezoelectric elements are simultaneously connected to the chip module substrate by using the base layer, heights of the connection elements do not need to be adjusted. Therefore a defect rate may be decreased due to simplification of the manufacturing procedure, and the manufacturing time may be reduced.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. An acoustic probe comprising:
a chip module substrate;
a piezoelectric unit for cross-converting ultrasound and an electric signal while the piezoelectric unit is vibrating; and
a connection unit for supporting the piezoelectric unit and electrically connecting the piezoelectric unit and the chip module substrate and formed of a material which has conductivity and acoustic impedance greater than acoustic impedance of the piezoelectric unit as a single layer, and
wherein the connection unit comprises a first surface electrically connected to the chip module substrate and a second surface in contact with the piezoelectric unit directly, wherein a size of the first surface and a size of the second surface are different from each other.

2. The acoustic probe of claim 1, wherein the size of the first surface is less than the size of the second surface.

3. The acoustic probe of claim 1, wherein the connection unit comprises at least one of tungsten carbide and graphite.

4. The acoustic probe of claim 1, wherein at least one of a greatest thickness and a smallest thickness of the connection unit is $\lambda(2n)$, where $\lambda$ is a frequency of ultrasound emitted from the piezoelectric unit, and n is a natural number.

5. The acoustic probe of claim 1, wherein the piezoelectric unit comprises a plurality of piezoelectric elements that are spaced apart from one other, and wherein the connection unit comprises a plurality of connection elements that are spaced apart from one other and support the plurality of piezoelectric elements, respectively.

6. The acoustic probe of claim 5, wherein at least one of the plurality of connection elements is stepped at least once.

7. The acoustic probe of claim 5, wherein a longitudinal cross-section of at least one of the plurality of connection elements has a T-shape.

8. The acoustic probe of claim 1, further comprising a bonding material disposed between the connection unit and the chip module substrate.

9. The acoustic probe of claim 8, wherein the bonding material comprises a conductive material.

10. The acoustic probe of claim 1, wherein the chip module substrate comprises a ultrasound-backing material.

11. The acoustic probe of claim 1, further comprising a ultrasound-backing unit disposed at a rear side of the chip module substrate and absorbing a part of ultrasound that is generated by the piezoelectric unit.

* * * * *